Aug. 16, 1960 J. S. REED Plant Pat. 1,967

AVOCADO

Filed April 7, 1959

INVENTOR.
JAMES S. REED
BY Fulwider, Mattingly & Hunter
ATTORNEY

United States Patent Office

Plant Pat. 1,967
Patented Aug. 16, 1960

1,967

AVOCADO

James S. Reed, 3767 Valley St., Carlsbad, Calif.

Filed Apr. 7, 1959, Ser. No. 804,855

1 Claim. (Cl. 47—62)

Figure 1:
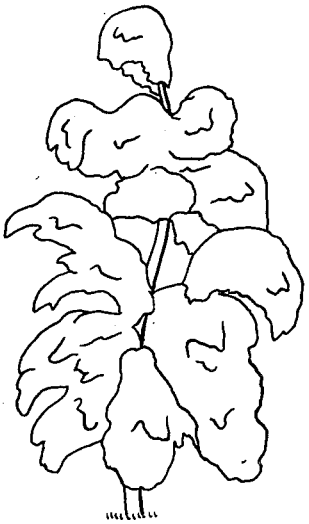

This invention relates to a new and improved variety of avocado plant which has many outstanding and desirable characteristics.

The original tree is a seedling planted about 1948 in an avocado grove owned by me at the corner of Magnolia and Valley Streets in Carlsbad, San Diego County, California.

I have successfully propagated this tree on Nabal, Fuerte, Dickerson, and Mexican seedling stock. The propagation has been asexually reproduced by successfully grafting scions of the tree of this application upon the aforementioned stock. Such grafting has occurred at 3767 Valley Street, Carlsbad, San Diego County, State of California. The location is approximately two miles east of the Pacific Ocean coastline at Carlsbad, California. This avocado has a very rapid growth and produces a tree of relatively medium height, ranging to about 20 feet and grows in a generally slender upward shape, rather than spreading out over large areas as do many avocados such as the Fuerte and Nabals. In general character this avocado seems more closely related to the Nabal than any other known variety. Wherever varieties of avocado are referred to in the foregoing paragraph or elsewhere in this specification, the applicant refers to "Hass" as the avocado covered by U.S. Plant Patent No. 139. The applicant believes no other varieties referred to are patented.

This avocado has a very distinct leaf shape, the leaves being dark green relatively slender, slightly crescent shaped and generally terminating in a relatively slender point. The veins in the leaves are not particularly pronounced and taken as a whole the leaf has a uniform appearance. The surfaces of the leaves which normally face upward and outward from the trunk of the tree are of a high gloss while the under surface has a flat appearance.

This avocado blooms late, generally after frost damage is principally past, blooming in the middle or latter part of March and setting in April. The fruit matures quite early in the year for summer fruit and is ready to be harvested in about April of the year following bloom.

The tree is found to be extremely resistant to frost damage. It has been observed that it will resist an ordinary frost temperature as low as 28° Fahrenheit which will harm other avocados and seems little affected by a mild frost.

The trees of this invention show a marked resistance to "salt burn" which makes it of particular desirability in coastal areas where salt burn frequently is a serious problem with other varieties. This tree has been observed in a grove of trees of other varieties at Carlsbad, California. The leaves of this tree remain virtually entirely green, while the varieties such as Fuerte, Nabal, Anaheim, and the like have leaves which turn brown and become brittle over a great portion of their surface, commencing from the tips.

The applicant has specifically noted that trees which have had sun blotch and located at the applicant's address in Carlsbad, California, and which have been cut back by the applicant and grafted to his variety have thereafter been free from sun blotch. The applicant has further noticed that adjoining trees particularly of Hass and other varieties mentioned in this application have had bad cases of sun blotch in the coastal area in San Diego County at the applicant's home where his experimentation has been carried on while his trees of this application are free from the same disease in the same area and under the same conditions.

The trees, as they grow, bear extremely large quantities of relatively small fruit. Fruit is spheroid in shape, averaging about 3 inches long and 8 to 10 ounces weight for each fruit. The trees bear large quantities economically marketable the second year after grafting. This results in early production from any grove.

The branches have a tendency to hang generally downward from the trunk and main branches contrary to a rather upward tendency towards the point of juncture which is exhibited by certain other varieties, notably the Nabal. This characteristic is important in that the branches dot not break under heavy loads as readily as would other varieties since there is a straight downward pull in the direction of growth which, of course, is quite resistant to breaking.

The fruit is characterized by a very high oil content; the oil content averaging in the neighborhood of 20%. The California Avocado Society of Los Angeles, California, analyzed fruit of this tree and found oil content 18.9%. The fruit has smooth, firm, buttery flesh with a nutty taste and is characterized by its ability to stay upon the tree for relatively long periods after having reached maturity. By this particular character, it is possible for a grower to maintain fruit for many weeks in order to take best advantage of price conditions as they occur.

Many avocados have a tendency to alternate—that is, to bear heavy one year and light another year, or heavy one year and light for two years. The avocado of this invention has proven itself to have a strong tendency to bear consistantly year after year and to have a strong tendency to eliminate the strong alternation found in many other varieties.

The skin is medium smooth, medium green color when mature, and it peels easily from the flesh. The green color is not an unusual green, but the customary green of several varieties of avocados such as Fuerte and Nabal, as distinguished from the dark purple of certain varieties such as Dickerson and Hass.

As well as having lasting qualities upon the tree as heretofore mentioned, this avocado, also, keeps well after harvesting for long periods thus making it possible to ship for long distances without danger of excessive loss.

The seed remains tight in the fruit until removed and is relatively small, weighing approximately ¾ of an ounce on the average. The seed is, in general appearance, the same as most avocado seeds and the seed coat adheres tightly to the seed itself so that when removed from the fruit it is not necessary to scrape out the seed coat prior to eating.

It is to be understood that the exact characteristics of the fruit will vary somewhat depending upon the individual care, fertilization, water, climatic conditions, etc., to which it is exposed in growing.

This avocado differs from the other avocados as heretofore specified and particularly in that:

It has a higher oil content than most other avocados;

It grows in a general tree shape somewhat similar to the Hass, but has green fruit, whereas the Hass is dark purple;

Bears heavily on limbs that hang generally downwardly from the major limbs or trunk, thus eliminating the tendency to break off.

The fruit differs from the fruit of other avocados in successfully combining the qualities of:

(1) Small size.
(2) High oil content.
(3) Slender shape of tree.
(4) Resistance to salt burn.
(5) Early maturity.
(6) Resistance to frost.
(7) Rapid growth and early bearing of newly grafted trees.
(8) Excellent keeping qualities.
(9) Resistance to sun blotch disease.

Figure 2:
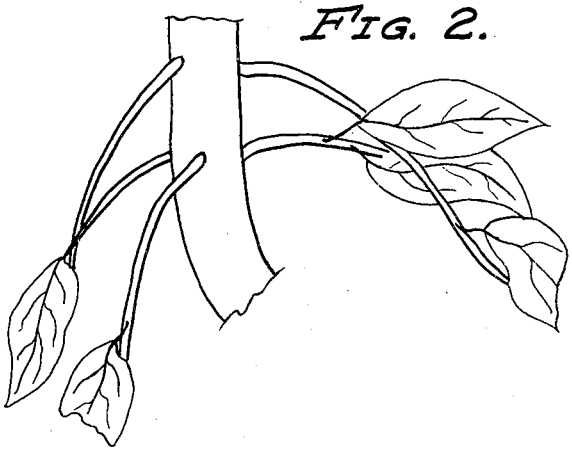
Figure 3:
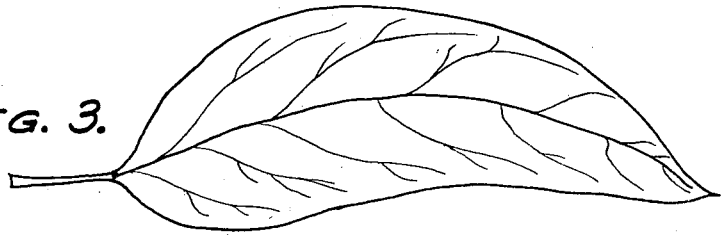
Figure 4:
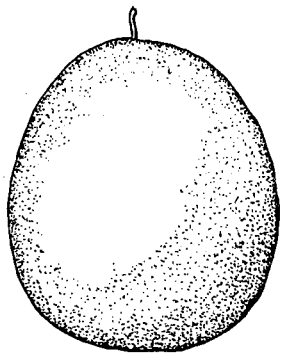
Figure 5:
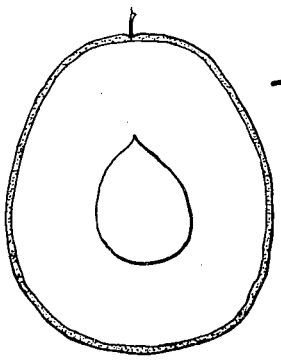

I have also attached hereto, as a part of this application, the following drawings:

Figure 1, the general shape of tree;

Figure 2, the characteristic attachment of limbs to trunk and major limbs;

Figure 3, leaf shape;

Figure 4, fruit shape;

Figure 5, sectionalized fruit shape.

I claim:

The variety of avocado tree described herein and particularly characterized by: April maturity, small size of fruit, slender shape of tree, high oil content of fruit, nutty flavor, smooth and creamy consistency of meat, consistently heavy bearing, good keeping quality of fruit, and resistance to frost, salt burn, and avocado sun blotch disease.

No references cited.